US004001610B2

United States Statutory Invention Registration [19]

[11] Reg. Number: H1610

Luo et al. [45] Published: Nov. 5, 1996

[54] METHODS FOR CULTURING HAIR FOLLICLE EPITHELIAL MATRIX CELLS

[75] Inventors: Xiaochun Luo, West Chester; Karen M. Lammers, North Bend; Monica L. Oltmanns, Cincinnati, all of Ohio

[73] Assignee: The Procter & Gamble Company, Cincinnati, Ohio

[21] Appl. No.: 162,516

[22] Filed: Dec. 3, 1993

[51] Int. Cl.[6] ..... C12N 5/02

[52] U.S. Cl. ..... 435/240.2; 435/240.21; 435/240.23; 435/240.243; 435/240.3; 435/240.31

[58] Field of Search ..... 435/240.2, 240.21, 435/240.23, 240.243, 240.3, 240.31

[56] References Cited

U.S. PATENT DOCUMENTS

| | | | |
|---|---|---|---|
| 4,254,226 | 3/1981 | Eisinger et al. | 435/240 |
| 4,919,664 | 4/1990 | Oliver et al. | 623/15 |
| 5,130,142 | 7/1992 | Wong et al. | 424/574 |
| 5,229,271 | 7/1993 | Philpott | 435/29 |

FOREIGN PATENT DOCUMENTS

| | | | |
|---|---|---|---|
| 107885 | 5/1984 | European Pat. Off. | A61K 7/06 |
| 4-99482 | 3/1992 | Japan | C12N 5/06 |
| 04169517A | 6/1992 | Japan | A61K 7/06 |
| WO92/07877 | 5/1992 | WIPO | A61K 7/06 |

OTHER PUBLICATIONS

Yuspa et al, NTIS patent application 07/048,537, filed May 6, 1987.

Warren et al., J. Invest. Dermatology, vol. 98, No. 5, pp. 693–699 (May 1992).

Parkinson, Seminars in Cell Biology, vol. 3 pp. 435–444 (1992).

Chang et al. PNAS (USA), vol. 79, pp. 4795–4799 (Aug. 1982).

Detmar et al, J. Invest. Dermatol. vol. 101; pp. 130S–134S (1993).

Frater, R. "In Vitro Differentiation of Mouse Hair Follicle Cells", *J. of Investigative Derm.*, vol.64, No. 4, pp. 235–239 (1975).

Frater, R. "A New Technique for Dissociation of Hair Follicles into Single Cells", *Experientia*, vol. 32, pp. 675–676 (1976).

Weterings, P. J. J. M., A. J. M. Vermorken and H. Bloemendal, "A Method for Culturing Human Hair Follicle Cells", *British J. of Derm.*, vol. 104, pp. 1–5 (1981).

Hewish D. R. and R. C. Marshall, "In Vitro Growth and Differentiation of Epithelial Cells Derived From Post–Embryonic Hair Follicles", *Aust. J. Biol. Sci.*, vol. 35, pp. 103–109 (1982).

Jones, L. N., K. J. Fowler, R. C. Marshall and M. L. Ackland, "Studies of Developing Human Hair Shaft Cells In Vitro", *The Society of Investigative Dermatology*, vol. 1, pp. 58–64 (1988).

Schaart, F. M., A. Mayer–da–Silva and C. E. Orfanos "Cultivation of Human Hair Follicle Cells", *Hair and Hair Diseases*, C. E. Orfanos and R. Happle, (eds) Chap. 13, pp. 301–324, (1989).

Philpott M. P., M. R. Green and T. Kealey "Human Hair Growth In Vitro", *J. of Cell Sci.*, vol. 97, pp. 463–471 (1990).

Kurata, S., S. Itami, T. Sonoda and S. Takayasu "Culture and Differentiation of Human Hair Matrix Cells In Vitro", *Abstracts, World Congress of Dermatology*, Jun. 12–18, NY (1992).

Reynolds, A. J., C. M. Lawrence and A. B. Jahoda "Human Hair Follicle Germinative Epidermal Cell Culture", *J. of Invest. Derm.*, vol. 101, No.4, pp.634–638 (1993).

*Primary Examiner*—Charles T. Jordan
*Assistant Examiner*—Chrisman D. Carroll

[57] ABSTRACT

The subject invention relates to methods of isolating, culturing and propagating epithelial matrix cells by removing/isolating the bulb region of a hair follicle directly above the dermal papilla, incubating the bulb in a pre-coated culture dish containing Chang medium supplemented with 10% fetal bovine serum, replacing the Chang medium with keratinocyte growth medium after 3-4 days, propagating the cells to the next passage after adding the keratinocyte growth medium and passing the pure epithelial matrix cells again to obtain a third passage of cells. The epithelial matrix cells may be passed for up to six passages, and are useful for screening potential hair growth actives.

3 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

METHODS FOR CULTURING HAIR FOLLICLE EPITHELIAL MATRIX CELLS

TECHNICAL FIELD

The subject invention relates to methods of isolating, culturing and propagating hair follicle epithelial matrix cells in vitro.

BACKGROUND OF THE INVENTION

Two groups of cells determine the structure of a hair follicle: dermal papilla (DP) cells and epithelial matrix (EM) cells. DP cells form an aggregate underneath the follicle. Their function includes providing regulating factors and nutrients to support proliferation and differentiation of the EM cells above them. EM cells have the function of proliferating and differentiating under the influence of DP cells and other environmental factors to give rise to the various parts of the hair follicle, including the hair shaft. Because EM cells play an important role in hair shaft production, major efforts have been undertaken to isolate and culture these cells in vitro. Cultured EM cells provide an ideal system to study the factors that affect hair follicle formation and hair shaft growth. Such cells also provide the opportunity for identifying and screening compounds for the treatment of hair-related diseases, including hair loss.

It is an object of the subject invention to provide methods for isolating, culturing and propagating EM cells in vitro.

It is a further object of the subject invention to provide in vitro methods of testing compounds for their involvement in hair regulation.

It is a still further object of the subject invention to provide in vitro methods for studying factors affecting hair follicle formation and hair shaft growth.

SUMMARY OF THE INVENTION

The subject invention relates to a method of isolating, culturing and propagating epithelial matrix (EM) cells, comprising the steps of:

a) micro-dissecting intact hair follicles from a human donor scalp;

b) cutting the bulb region of each hair follicle within about 50 microns or less above the dermal papilla (DP), which is an aggregate of cells surrounded by a membrane;

c) pre-coating a culture dish surface with a supporting matrix selected from type I collagen, type IV collagen, fibronectin, and mixtures of basement membrane proteins and other extracellular matrix proteins;

d) adding Chang medium supplemented with 10% fetal bovine (fetal calf) serum to the culturing dish;

e) placing the bulb (comprising the EM cells and DP) in the pre-coated culture dish containing Chang medium;

f) growing the cells for 3–4 days;

g) replacing the Chang medium with keratinocyte growth medium (KGM);

h) passing the cells at a ratio of about 1:2 to about 1:3, 4–6 days following addition of the KGM medium to a second passage;

i) passing the pure EM cells again after 4–7 days to a third passage; and j) passing the EM cells for up to six passages, as needed.

The EM cells thus cultured are useful in screening tests for potential hair growth actives. For example, the level of EM cell proliferation can be measured following treatment of cultured EM cells with a compound of interest. In another method, the level of hair specific keratin proteins, produced by EM cells, can be measured following the treatment of cultured EM cells with a compound of interest.

The EM cells thus cultured are also useful for studying factors affecting hair follicle formation and hair shaft growth.

DETAILED DESCRIPTION OF THE INVENTION

As used herein, "EM" refers to epithelial matrix.

As used herein, "DP" refers to derreal papilla.

As used herein, "type I collagen" refers to an extracellular matrix protein available from Collaborative Biomedical Products (Bedford, MA).

As used herein, "type IV collagen" refers to an extracellular matrix protein available from Collaborative Biomedical Products (Bedford, MA).

As used herein, "fibronectin" refers to an extracellular protein available from Collaborative Biomedical Products (Bedford, MA).

As used herein, "basement membrane proteins" refers to a mixture of proteins located at the interface of epithelial and mesenchymal cells assumed to contain the extracellular subset of factors affecting epithelial and mesenchymal interactions.

As used herein, "extracellular matrix proteins" refers to a mixture of proteins filling the outer space of cells.

As used herein, "Chang medium" refers to human amniotic cell culture medium obtained from Irvine Scientific, Inc. (Santa Ana, CA).

As used herein "fetal bovine serum" refers to a serum available from HyClone, Inc. (Logan, UT).

As used herein, "KGM" refers to keratinocyte growth medium available from Clonetics, Inc. (San Diego, CA).

As used herein "passing cells at a ratio of 1:X" refers to splitting one dish or well of cells into X dishes or wells for further growth.

As used herein, "regulating hair growth" means increasing the level of hair specific keratin protein production, and/or inducing the formation of a greater number of hair strands, and/or increasing the diameter of the hair strand, and/or lengthening the hair strand, and/or preventing, retarding or arresting the process of hair loss, and/or increasing the size of the hair bulb, and/or increasing the number of EM cells.

As used herein, "anagen phase" refers to the period in the hair follicle growth cycle wherein the follicle is actively growing and producing new hair.

As used herein, "telogen phase" refers to the period in the hair growth cycle wherein the follicle is resting and not producing new hair.

As used herein, "confluence" means that the cells are covering a given percentage of the culture dish. When cells cover the desired percentage of the culture dish, they are divided into 2–5 dishes for further growth.

METHOD FOR CULTURING HAIR FOLLICLE EPITHELIAL MATRIX CELLS

The subject invention relates to a method of isolating, culturing and propagating EM cells for further in vitro study.

Micro-Dissection of the Intact Hair Follicles From a Donor Scalp

A piece of scalp tissue (obtained, for example, from a cosmetic surgeon) is cut into a strip from about 2 mm to about 5 mm wide, preferably from about 2 mm to about 4 mm wide, most preferably about 3 mm wide; and from about 5 mm to 100mm long, preferably from about 20 mm to about 50 mm long, also preferably about 20 mm long. The white epidermal layer is separated from the underlying fat layer. The fat layer which contains the lower part of the anagen follicles is used for dissection after completely removing the epidermal layer such that the follicles can be pulled out intact. The follicles are plucked and placed in a separate dish containing fresh Chang medium.

Isolation of the Bulb Region of Each Follicle

The lower half of the hair bulb is cut between the dermal papilla (DP) and the pigmented shaft within about 50 microns above the DP, preferably within about 10 microns above the dermal papilla, more preferably within about 2 microns above the dermal papilla. The resulting bulb contains the DP, the EM cells, some melanocytes and a minimal amount of hair shaft. All of the above components are enclosed by the dermal sheath.

Subject tests indicate that where the bulb is cut off the follicle is critical to the success of subsequent EM cell out-growth. The optimal place to remove the bulb from the follicle is right above the dermal papilla. If the cut is made too high above the DP, the presence of the hair shaft significantly hampers the rate of outgrowth of EM cells. If the cut is made too low into the bulb, EM cells are lost. The out-growth rate of the EM cells from the hair follicle can be as high as 100% if the cutting point is in the correct position.

Initial Incubation of Cells for 3–Days

The bulbs are transferred to a pre-coated culture plate that also contains Chang medium. The follicles are cultured under standard conditions (at about 30°–42° C. and about 90–93% humidity in about 5% $CO_2$). Suitable coating materials include, but are not limited to, type I collagen, type IV collagen, fibronectin, and EHS (Engelbreth-Holm-Swarm tumor) basement membrane (obtained from Collaborative Biomedical Products, Bedford, MA). EM cells can out-grow on all the above materials as well as on a plastic surface. Preferred coating materials include EHS basement membrane, type I collagen and type IV collagen gel; more preferred materials include EHS basement membrane and type I collagen gel; also preferred coating materials include EHS basement membrane.

Chang medium, a high serum and high calcium medium, best supports the initial out-growth of the EM cells. Chang medium not only promotes the adherence of the hair follicle bulb to the bottom of the culture dish, but also encourages out-migration and initial proliferation of EM cells. Another potential medium is Dulbeco's Modified Eagle Medium (DMEM), obtained from Clonetics, Inc. (San Diego, CA), which encourages follicle adherence but has limited ability to promote out-growth. KGM is less suitable for initial cell growth because it prevents hair follicles from adhering to the culture dish.

Replacement of Chang Medium with KGM

After about 72 to about 110 hours of incubation, the Chang medium is replaced by KGM, which encourages further proliferation of EM cells by allowing them to continue expanding. An EM cell colony cannot be expanded long-term (over about 5 days) by continuing to incubate in Chang medium. Chang medium causes cells to aggregate together, impeding further proliferation, because it has a high calcium content. Reducing the calcium level is crucial after the initial treatment with the Chang medium. KGM is a serum-free, low calcium medium designed for keratinocyte growth.

Propagation of EM Cells to the Next Passage

The EM cells are washed with a suitable buffer, for example HEPES-buffered saline solution (Clonetics, Inc.) and treated briefly, at about 37° C., with trypsin/EDTA (Clonetics, Inc.) to cleave the protein bonds attaching the cells to the bottom of the plate. The trypsin is then neutralized with trypsin neutralizing solution (obtained from Clonetics, Inc.), or bovine serum albumin. The cell suspension is transferred to a centrifugation tube and centrifuged at 2000 rpm. The supernatant is removed and the remaining cell pellet is washed with 2 to 50 mls of phosphate-buffered saline (PBS) or KGM to prevent further proteolysis. The cell pellet is re-suspended in KGM and the suspension dispensed to a different plate at a ratio of about 1:2 to about 1:3, by increasing the number of plates from 1 to 2 or 3. A second generation of pure EM cells is thus obtained.

Pure EM cells are similarly passed to the next generation after about 4 to about 7 days. Subsequent passages can be similarly performed, as necessary. Up to 6 passages of cells can be obtained in this manner.

Uses of Cultured Cells

Cultured EM cells can be used for a variety of purposes. They can be used to screen and identify hair growth compounds. EM cells can also be used to understand the mechanism of hair growth regulation.

In screening tests, EM cells can be treated with test compounds and their increase in proliferation measured by known methods such as $^3H$ thymidine incorporation. For a detailed description, see Ristow and Messmer, J. of Cell Physiol., Vol. 137, p. 277 (1988) or Ristow, J. of Invest. Dermatol., Vol. 79, p. 408 (1982), incorporated herein by reference. Keratin ribonucleic acid assays can also be used, whereby EM cells are treated with test compounds and the change in the level of hair specific keratin ribonucleic acid is measured by polymerase chain reaction (PCR). For a detailed description of the PCR procedure, see Innis, M. A., D. H. Gelfand, J. J. Sninsky and T. J. White, PCR Protocols: A Guide to Method and Application, (Cetus Corporation: Emeryville, CA) (1990); incorporated herein by reference.

EM cells can also be used to study mechanisms of hair growth regulation. Limited examples include (i) identification of growth factors affecting EM cell proliferation and elucidation of their roles in hair growth;

(ii) study of factors regulating EM cell differentiation and the relationship between differentiation and proliferation;

(iii) comparison of the difference between EM cells of normal versus balding and transitional hair follicles;

(iv) study of the effect of steroid hormones, including androgen on the proliferation, differentiation, morphology and biochemistry of EM cells, and their roles in hair growth regulation;

(v) study of the differences between EM cells and other epithelial cells and the biological mechanism behind the differences.

The following example is intended to illustrate the subject invention without limiting the same.

A sharp instrument, such as a pair of scissors, is used to cut a strip of scalp tissue (obtained from a cosmetic surgeon) approximately 3 mm wide and 30 mm long. The white epidermal layer is separated from the underlying fat layer by cutting between the two layers with a pair of toothed scissors. The fat layer containing the lower part of the anagen follicles is used for dissection. The epidermal layer is discarded. The epidermal layer should be completely removed so that the follicles can be pulled out intact.

To separate the follicles cleanly from the fat layer, one pair of forceps is used to hold the fat layer in place. A second pair of forceps is used to pull the anterior end of the follicle to release the follicle intact from the fat layer. The plucked follicles are placed in a separate dish in fresh Chang medium.

The lower half of the hair bulb is cut with micro-scissors between the dermal papilla and the pigmented shaft within about 2 microns above the DP. The resulting bulb contains the DP, the EM cells, some melanocytes and a minimal amount of hair shaft. All of the above components are enclosed by the dermal sheath.

The bulb is transferred to a 24 well culture plate containing Chang medium, pre-coated with EHS basement membrane (Collaborative Biomedical Products). About ten follicles are placed in each well of the 24 well plate. The follicles are cultured at 37° C and 5% $CO_2$ and 90–93% humidity. After about 72–96 hours of incubation, the cultures are examined under a microscope, and the medium/ changed to KGM.

The cells are passed to a second passage when they reach 75% confluence (normally 7–10 days after dissection). The cells are washed once with about 0.5 ml HEPES buffer (Clonetics, Inc.) per well. Then about 0.2 ml of trypsin/ EDTA (Clonetics, Inc.) is added in the well followed by an approximately 3 minute incubation at about 37° C. About 0.4 ml of trypsin neutralizing solution (Clonetics, Inc.) is added to the cells and centrifugation is performed. The supernatant is removed and about 10 ml PBS added to wash the cell pellet. Centrifugation is repeated and the supernatant removed.

The cell pellet is re-suspended into KGM at a total volume of 1–2 ml per well. After dispersion of the pellet, additional KGM is added to adjust the density of the EM cells. The cell suspension is dispensed to a new 24 well plate at about 1 ml per well. The passage is done at a 1:3 ratio of the original number of wells to the resultant number of wells. The pure EM cells are passed again after 4–7 days to obtain a third passage of cells.

What is claimed is:

1. A method of isolating and culturing epithelial matrix cells, comprising the steps of:

a) micro-dissecting intact hair follicles, wherein the hair follicles comprise a bulb region, the bulb region comprising dermal papilla cells and epithelial matrix cells, wherein the epithelial matrix cells exist above the dermal papilla cells and the dermal papilla cells exist proximate to the base of the bulb region;

b) cutting the bulb region of each hair follicle to remove the bulb region from the follicle, the bulb region being cut within about 50 microns or less above the dermal papilla cells to form a cut bulb region comprising epithelial matrix cells and the dermal papilla cells;

c) placing the cut bulb region in a culture plate containing Chang medium;

d) allowing the cut bulb region to form new epithelial matrix cells for about 4 to 6 days;

e) replacing the Chang medium with a medium suitable for keratinocyte growth which allows the proliferation of new epithelial matrix cells beyond the period of step (d);

f) passing the new epithelial matrix cells 4–6 days following addition of the medium suitable for keratinocyte growth by i) treating the new epithelial matrix cells with trypsin and EDTA to detach the new epithelial matrix cells from the bottom of the culture plate;

ii) neutralizing the trypsin; and iii) dispensing the new epithelial matrix cells to a new plate to obtain a second passage of pure epithelial matrix cells; and g) passing the pure epithelial matrix cells obtained from step (f) to a third passage.

2. A method of screening a potential hair growth compound for activity comprising measuring change in proliferation of epithelial matrix cells after addition of a hair growth compound to the epithelial matrix cells, wherein the epithelial matrix cells are obtained according to the method described in claim 1.

3. A method of screening a potential hair growth compound for activity comprising measuring change in level of hair specific keratin ribonucleic acid of epithelial matrix cells after addition of the hair growth compound to the epithelial matrix cells, wherein the epithelial matrix cells are obtained according to the method described in claim 1.

* * * * *